United States Patent
Deblasi et al.

[11] Patent Number: 6,036,945
[45] Date of Patent: Mar. 14, 2000

[54] DELIVERY SYSTEMS FOR ACTIVE INGREDIENTS INCLUDING SUNSCREEN ACTIVES AND METHODS OF MAKING SAME

[75] Inventors: Douglas S. Deblasi, Fairfield; Manshi Sui, Hillsborough; Roy Pe, Kendall Park, all of N.J.

[73] Assignee: Shamrock Technologies, Inc., Newark, N.J.

[21] Appl. No.: 08/843,032

[22] Filed: Apr. 11, 1997

[51] Int. Cl.[7] ............................................. A61K 7/44
[52] U.S. Cl. ........................ 424/59; 424/60; 424/69; 424/78.03; 424/78.32; 424/489
[58] Field of Search ........................ 424/59, 60, 69, 424/78.03, 78.32, 489

[56] References Cited

U.S. PATENT DOCUMENTS

| | | | |
|---|---|---|---|
| 5,468,477 | 11/1995 | Kumar et al. | 424/78.17 |
| 5,480,632 | 1/1996 | Orr et al. | 424/63 |
| 5,691,327 | 11/1997 | Blank | 514/159 |
| 5,700,452 | 12/1997 | Deckner et al. | 424/59 |
| 5,700,472 | 12/1997 | Deckner et al. | 424/59 |
| 5,714,134 | 2/1998 | Richard et al. | 424/59 |

Primary Examiner—Jose' G. Dees
Assistant Examiner—Kathryne E. Shelborne
Attorney, Agent, or Firm—Baker & Botts, LLP

[57] ABSTRACT

The present invention provides methods of making delivery systems for active ingredients including hydrogenated jojoba and sunscreen actives. The recrystallization process of the present invention produces small particle size alloys from molten mixtures and recrystallized small particle size dispersions from high temperature solvent solutions. The invention further provides delivery systems for active ingredients such as sunscreen actives.

42 Claims, No Drawings

DELIVERY SYSTEMS FOR ACTIVE INGREDIENTS INCLUDING SUNSCREEN ACTIVES AND METHODS OF MAKING SAME

FIELD OF INVENTION

This invention relates to processes for producing small particle size powder alloys from molten mixtures and for producing recrystallized small particle size dispersions from high temperature solvent solutions. These alloys and dispersions are useful in both clear and color formulations for personal care preparations, especially cosmetics and particularly cosmetic sunscreen formulations. In addition, this invention relates to the use of selected cosolvents in the process of recrystallization to form small particle size dispersions. Moreover, this invention relates to the inclusion of an insoluble nucleating agent in the recrystallization process to enhance small size crystal growth as well as dispersion processing, and to improve the formula properties of the powder alloys and recrystallized dispersions. Furthermore, this invention relates to the use of the disclosed processes to prepare improved personal care formulae, especially improved cosmetics formulae, and in particular improved sunscreen formulae and sunscreen-containing cosmetic formulae.

BACKGROUND OF THE INVENTION

The recrystallization of polar solutes with marginal solubility in non-polar solvents is known. For relatively pure solutes, enhancing solubility by increasing the temperature of the solvent may be sufficient to effect a suitable recrystallization result. However, conventional methods of recrystallization may be unsuitable for mixtures in which impurities are present, or more than one solute is employed, or an insoluble substance is present during recrystallization, since the nature of mixtures is to prevent or retard crystal growth of selected ingredients. As a result, small size crystals and small size dispersed particles cannot be consistently and reproducibly obtained using conventional recrystallization techniques.

The recrystallization of organic solids to produce small crystals, leading to powders and dispersions of small particle size, i.e., ranging from less than one to about twenty-five microns, is important in several formulation-based industries. As used herein, a formulation-based industry is an industry whose products are based on mixtures of ingredients, in which each ingredient retains most of its original chemical properties despite being combined with the other ingredients. Such industries include, but are not limited to, those which produce personal care products, cosmetics, and over-the-counter drug formulations such as antiperspirants and sunscreens.

Conventional dispersion methods such as high speed, high shear stirring and solvent recrystallization are widely used in these industries, but these methods do not readily create a uniform dispersion of very small particle size unless the solid component has been micronized by prior processing, or has undergone purification processing, or has been processed through expensive and time-consuming specialized equipment, e.g., high-pressure homogenizers.

Therefore, there exists a need in the formulation-based industries to reduce the particle size of certain ingredients, and to formulate with such ingredients in either powder form or dispersed form, without premicronization or purification processing or specialized equipment. This has become especially evident in the personal care and cosmetics industries, the latter in particular for the formulation of sunscreens and cosmetics containing sunscreens.

Due to the increasing use of both natural and synthetic organic ingredients, the personal care industries and especially the cosmetics industry have recently been seeking a greater degree of perceived topical benefits from products applied directly onto the stratum corneum. These benefits include lubricity, evenness of application, spreadability, lack of oiliness or stickiness, greater skin adhesion and a more comfortable, even pleasant, skin feel.

Thus, a need exists in the cosmetics and personal care industries for new formulations of fine particle size powders and dispersions, and for processes to produce such formulations that are efficient, effective, and yield products with a uniform particle size that are comfortable to use. In the case of cosmetics, sunscreens and sunscreen-containing cosmetics, a need exists for formulations that are lubricous, have a non-oily, non-greasy, non-sticky, pleasant skin feel, and are efficacious in that the expected Sun Protection Factor ("SPF") value of a sunscreen formula is not impaired.

Accordingly, it is an object of the present invention to provide improved processes for producing small particle size powders, and recrystallized mixtures and dispersions of small crystal size, that function as active ingredient delivery systems within the types of industries described.

Another object of the invention is to provide an improved process by which to recrystallize an insoluble active ingredient, thereby affording the formulator substantial ease of use when incorporating such an active ingredient into finished product formulae.

Still another object of the invention is to provide improved fine particle size powders, mixtures and dispersions.

A further object of the invention is to provide improved topical ingredients for personal care products such as cosmetics and sunscreens that are lubricous and aesthetically pleasing to the skin.

Yet another object of the invention is to provide lubricous mixtures that are efficacious, particularly in the active ingredient delivered.

SUMMARY OF THE INVENTION

The present invention employs chemical means of enhancing solubility at elevated temperature, followed by rapid cooling to induce recrystallization from a solution or from the molten state, as well as optional fine particle nucleation. As a result, neither premicronization, nor high purity, nor special equipment is required in order to produce powder mixtures and dispersions of small particle size.

In accordance with one embodiment of the present invention, a process for producing via recrystallization powder alloys of small particle size, for use in both color and clear formulations in personal care products and the like, comprises the steps of combining at least one first solid organic wax lubricant (lubricating wax), with at least one active ingredient. An active ingredient is a compound having physical and/or chemical characteristics which would be considered necessary or desirable in a finished product (i.e., the compound would be useful as an active ingredient of the finished product), provided that the compound could be introduced or delivered in a usable form, that is, as a powder or as a dispersion incorporating very small size particles of the compound.

Active ingredients useful in the present invention include those that may be useful in a personal care product, such as hydrogenated jojoba, or such as a material that is capable of absorbing and/or blocking ultraviolet light and which is therefore useful in sunscreen formulations and in sunscreen-containing cosmetic formulations (referred to herein as "sunscreen actives"). In accordance with the present invention, the active ingredients can be delivered as a wax alloy powder, rather than as the more common form, an emulsion. Emulsions are conventional in the prior art but are susceptible to weakening or destruction of desirable physical properties when a formulation containing the emulsion is spread upon the skin.

In this embodiment of the invention, the sunscreen active or hydrogenated jojoba is selected as the active ingredient. Since most organic wax lubricants are non-polar and therefore not directly miscible with hydrogenated jojoba or with a polar organic sunscreen active, even at elevated temperatures, the other component of the alloy, the solid organic wax lubricant, is selected from a group of polar waxes having chemical structures that impart the above-described desired physical properties to the resulting alloy powder.

The solid organic wax lubricant and the active ingredient are heated together to an elevated temperature with stirring, after which the molten alloy solution is cast as a thin sheet and thereby cooled. As used herein, the term "stirring" is meant to encompass any appropriate means for agitation that is known to those skilled in the art. The resulting solid is subsequently milled, for example by chopping and then micronizing to a fine particle size in a fluid energy mill or any other appropriate fine particle-producing mill, yielding a powder alloy which, when incorporated into a formulation that is spread upon the skin, retains all of the desirable physical properties of the wax lubricant and also retains the efficacy of the sunscreen active or the hydrogenated jojoba.

In accordance with another embodiment of the present invention, the deficiencies of the prior art recrystallization techniques are overcome by adding a selected cosolvent at ambient or elevated temperature and by controlling the cooling rate such that small size crystals are produced even when impurities are present.

More specifically, in this embodiment the solid organic wax lubricant and the active ingredient are melted and dissolved with stirring in at least one liquid solvent, in which either the solid organic wax lubricant alone or the active ingredient alone is not ordinarily soluble, even at elevated temperature. Thus, each component of the wax lubricant/active ingredient pair is considered to be the "cosolvent" of (or in the alternative, to be a wetting agent for) the other component of the pair. The mixture is heated to an elevated temperature, for example, from about 60° C. to 175° C. in order to effect a miscible, clear solution. When that solution is cooled rapidly from the elevated temperature range to a non-elevated temperature range, for example from about 25° C. to about 50° C., recrystallization takes place, yielding a pasty wax alloy dispersion consisting of mixed crystals of the organic wax lubricant and active ingredient, the mean particle sizes of which range from below one micron to about twenty-five microns, and typically from about one micron to about eight microns.

The foregoing embodiments of the present invention include the optional addition of an insoluble nucleating agent, either to the melt blend of the solid organic wax lubricant and active ingredient, or to the solution of the solid organic wax lubricant, active ingredient, and non-polar liquid solvent. Suitable nucleating agents include titanium dioxide or an insoluble, micronized fluoropolymer such as polytetrafluoroethylene, having a particle size of ten microns or less. The nucleating agent is added with stirring while maintaining the mixture within the elevated temperature range, followed by cooling the mixture rapidly to a non-elevated temperature range. The optional use of a nucleating agent allows even smaller size crystals to be produced from solution, yielding a recrystallized wax alloy dispersion, the mean particle sizes of which range from below one micron to about five microns.

The processes disclosed herein produce recrystallized mixtures which provide formulators with advantageous, finer particle size ingredients than would be available from conventional methods. In addition, due to the rapid cooling step described, greater efficiencies for producing very fine crystals are realized.

The processes of the invention, and the micronized recrystallized solids and recrystallized dispersions that are produced, facilitate the formulation of personal care products, especially cosmetics and sunscreens, in which fine particle size waxes contribute to a lubricous, aesthetic skin feel and to the efficacious application of active ingredients found in sunscreens. The resulting mixtures, whether micronized recrystallized solids or recrystallized dispersions, are also advantageous to formulators as delivery systems for such active ingredients.

The present invention provides a lubricating wax product, containing particles of very small size, which may either be a fine micronized powder derived from a recrystallized melt blend, or a paste derived from a recrystallized dispersion when a solvent is used.

The method of the present invention may be used to form recrystallized wax alloys that incorporate active sunscreen ingredients and which may be incorporated into finished sunscreen formulations, the expected SPF value of which will not be impaired, and may be enhanced.

The cosmetic and sunscreen formulations produced by the method of the present invention are lubricous and provide excellent skin adhesion and water resistance as well as other tactile properties that make them comfortable and pleasant to use.

DETAILED DESCRIPTION OF THE INVENTION

The processes of this invention and the specific components selected produce a lubricating wax mixture. That mixture may either be a fine micronized powder derived from a recrystallized melt, or it may be a recrystallized fine particle size dispersion in cases in which a solvent is used.

In accordance with one embodiment of the present invention, the solid organic wax lubricant is combined directly with the active ingredient in the manner set forth hereinafter. The active ingredient may be a sunscreen active or it may be hydrogenated jojoba. Hydrogenated jojoba is a polar material that is useful as an emollient or skin softener in cosmetic formulations. The sunscreen active may be any one or more of a number of polar organic substances that absorb ultraviolet light and that are either liquids or solids at room temperature, or it may be any one or more of several inorganic solids which block or scatter ultraviolet light. The selection of the sunscreen active will depend upon several factors, including compatibility with potential candidates for the solid organic wax lubricant in the formation of a miscible melt at elevated temperatures, and the intended end use for the resulting wax-containing mixture.

Suitable organic sunscreen actives include aminobenzoic acid, cinoxate, diethanolamine methoxycinnamate, digalloyl trioleate, digalloyl trioleate, dioxybenzone, ethyl 4-[bis (hydroxypropyl)]aminobenzoate, glyceryl aminobenzoate, homosalate, lawsone with dihydroxyacetone, menthyl anthranilate, octocrylene, octyl methoxycinnamate, octyl salicylate, oxybenzone, padimate O, phenylbenzimidazole sulfonic acid, red petrolatum, sulisobenzone and trolamine salicylate, all of which are considered "Category I" sunscreen actives and are considered "approved for use" according to the U.S. Food and Drug Administration's Tentative Final Monograph published on May 12, 1993. Also, cinnamic acid derivatives, including but not limited to 3-(4-hydroxy-3-methoxyphenyl)-2-propenoic acid (a cinnamic acid derivative which is also known as ferulic acid, and which may be derived in a known manner from a natural extract of rice) and esters thereof (e.g., the ethyl ester of ferulic acid, hereinafter referred to as "ethylferulate"), benzoic acid derivatives, including but not limited to substituted benzoyl compounds (e.g., 4-tert-butyl-4'-methoxydibenzoylmethane, also known as avobenzone) and esters thereof, salicylic acid derivatives and esters thereof, and other suitable carboxylic acid derivatives and esters thereof, may be selected. Therefore, the scope of the invention is not limited to the organic Category I sunscreen actives.

Suitable inorganic sunscreen actives may be selected from either titanium dioxide (also a Category I sunscreen active) or zinc oxide, or both in combination, with a primary particle size that is in the range of 20–100 nanometers, and is preferably about 30 nanometers.

In the cases in which the active ingredient is a polar material, e.g., hydrogenated jojoba or one of the organic sunscreen actives, the solid organic wax lubricant may be selected from among one or more of the following polar lubricating waxes: oxidized polyethylene, erucamide, ethylenebisstearamide, carnauba wax, candellila wax, montan wax and glycerolmonostearate. The preferred polar waxes are oxidized polyethylene (e.g., Acuscrub 392, which is available from Allied Chemical Corporation of Morristown, N.J.) and ethylenebisstearamide. Examples of specific pairs of materials that may benefit from the present invention include, but are not limited to, etyhlenebisstearamide with ethylferulate, ethylenebisstearamide with hydrogenated jojoba, ethylenebisstearamide with avobenzone, oxidized polyethylene with ethylferulate, oxidized polyethylene with oxybenzone, glycerolmonostearate with ethylferulate, and ethylenebisstearamide with octyl methoxycinnamate.

In the cases in which the active ingredient is an inorganic sunscreen active, the solid organic wax lubricant may be selected from a wider range of materials, including one or more of the following polar and non-polar lubricating waxes: polyolefins of low to medium molecular weight (e.g., 300 to 18,000, when calculated according to the number-average method), such as polyethylene, polymethylene and polypropylene, as well as oxidized polyethylene, oxidized polypropylene, glycerolmonostearate, paraffin wax, candellila wax, carnauba wax, ethylenebisstearamide, montan wax, erucamide, microcrystalline wax and the like.

In cases in which the active ingredient is a solid organic sunscreen active (such as ethylferulate), the lubricating wax is present in an amount ranging from about 10% to about 75% by weight, and preferably from about 25% to bout 60% by weight, and the sunscreen active is present in an amount ranging from about 25% to about 90% by weight, and preferably from about 40% to about 75% by weight.

The solid organic wax lubricant and active ingredient are added to a heating vessel and are heated together with stirring to a temperature in the range of from about 70° C. to about 150° C. until a clear molten alloy is formed. Alternately, the wax lubricant is heated to the elevated temperature until a liquid is formed, and the active ingredient is then added while maintaining the temperature of the liquid in the range of from about 70° C. to about 150° C. The molten alloy is cooled, for example by casting as a thin sheet in a heat conductive tray and thereby cooling to ambient temperatures, thus achieving a hardened state in most cases in about ten minutes or less. In some cases, however, hardening may not take place readily upon cooling, such as when the active ingredient is of relatively low purity, which is especially commonplace when it is derived from a naturally-occurring substance. In these cases it may be necessary to allow the cast sheet to harden over the course of one to seven days under ambient conditions. In the alternative, the hardening can be accelerated by lowering the temperature of the cast sheet still further, to a temperature in the range of from about −20° C. to about −35° C., for example in a mechanical freezer, in order to insure more rapid hardening of the alloy, usually within about 24 hours.

The hardened alloy is then milled, for example by chopping in a mechanical chopper and micronizing in a fluid energy mill or any other appropriate fine-particle producing mill to less than ten microns mean particle size. When formulated into a sunscreen product, this wax alloy is lubricous on the skin, feels pleasant to apply and is efficacious in SPF value relative to the amount of the sunscreen active in the formula. Formulations can easily be prepared with the present wax alloy. In contrast, most solid organic sunscreen actives, such as ethylferulate, are difficult to use in preparation of formulations, are abrasive on the skin, and cannot be micronized into a powder due to their low melting points.

In cases in which the active ingredient is a liquid organic sunscreen active, such as octylmethoxycinnamate, the lubricating wax is preferably present in an amount ranging from about 40% to about 90% by weight, and the sunscreen active is preferably present in an amount ranging from about 10% to about 60% by weight. In all other respects, the process is the same as set forth above for the solid organic sunscreen actives, except that the ingredients are heated with stirring until a clear homogeneous solution is formed. The resulting recrystallized mixture contains very fine droplets of the liquid sunscreen active.

In cases in which the active ingredient is an inorganic sunscreen active, such as titanium dioxide, the lubricating wax is preferably present in an amount ranging from about 50% to about 90% by weight, and the sunscreen active is preferably present in an amount ranging from about 10% to 50% by weight. Also, the lubricating wax is first heated alone with stirring, to a temperature in the range of from about 100° C. to about 175° C. (the temperature chosen will depend upon the melting point and the viscosity of the selected wax) to form a liquid melt; the melt viscosity should be low enough to allow the selected inorganic sunscreen active to be added slowly to the stirred melt over 10 to 30 minutes to form a uniform dispersion. In all other respects, however, the process is the same as set forth above for the solid organic sunscreen actives. The resulting solid dispersion of an inorganic sunscreen active in a recrystallized lubricating wax dispersion is lubricous on the skin and can be used directly in a sunscreen formulation.

In cases in which the active ingredient is hydrogenated jojoba, both that ingredient and the organic wax lubricant are present in an amount ranging from about 1% to about 99% by weight. In a cosmetic application, the amount of hydrogenated jojoba will vary directly with the level of emolliency that is desired in the final product, and the amount of lubricating wax will vary directly with the level of skin lubricity and aesthetic skin feel that is desired in the final product. These materials are heated together with stirring to a temperature in the range of from about 60° C. to about 150° C. In all other respects, however, the process is the same as set forth above for the solid organic sunscreen actives.

In accordance with another embodiment of the invention, at least one liquid solvent may also be used in the present method. The liquid solvent is selected from among one or more of the following: glycerine, polydecene, hydrogenated polyisobutene, jojoba oil, dipropyleneglycolmonomethylether and petrolatum-based fractionated solvents such as mineral oil, petrolatum, liquid fractions of isoparaffin wax and Magie 47 (trade name for a product of the Magie Bros. division of Penzoil Corporation of Tulsa, Okla.). Other suitable solvents include linseed oil, butylcarbitol and the like. The preferred solvents are non-polar solvents including polydecene, hydrogenated polyisobutene, and either Magie 47 or another petroleum-based fractionalized solvent.

In embodiments of the present invention in which a solvent is included, the selection of the solvent depends upon several factors, including compatibility with the selected solid organic wax lubricant in the formation of a solvent solution at elevated temperatures, and the intended end use for the resulting wax-containing mixture. In cases in which the active ingredient is a solid organic sunscreen active, the lubricating wax is present in an amount ranging from about 10% to about 40% by weight, the sunscreen active is present in an amount ranging from about 10% to about 40% by weight, and the solvent is present in an amount ranging from about 20% to about 80% by weight.

These materials are added to a heating vessel and are heated with stirring for 30 minutes±10 minutes to a temperature in the range of from about 70° C. to about 175° C., and preferably from about 100° C. to about 150° C., to form a clear solution. Alternately, the active ingredient may be added subsequent to heating while maintaining the temperature in the elevated range. The solution of wax, solvent, and sunscreen active is then cooled rapidly by mechanical means, such as in an ice water bath for a period of between about 0.1 minutes and about 10 minutes, and preferably in a wiped film heat exchanger, in which case the solution is preferably cooled only for a period of between about 0.01 minutes and about 2 minutes.

The solution is cooled to a non-elevated temperature in the range of from about 25° C. to about 50° C., and preferably below 32° C., and during this cooling recrystallization occurs. The resultant dispersion has a pasty consistency, similar to that of toothpaste or peanut butter, and the mean particle size in the dispersion is less than ten microns, typically less than five microns.

In this embodiment of the invention, if, for example, ethylferulate is selected as the active ingredient, then the lubricating wax acts as a cosolvent, since ethylferulate by itself is not soluble to any significant extent in any of the preferred solvents. Thus, this embodiment of the present invention solves a significant problem which the prior art has heretofore been unable to overcome without emulsification, namely, the poor solubility of ethylferulate and other polar solid organic sunscreen actives in non-polar solvents, which causes difficulties in formulating sunscreen products in non-emulsified systems. Further, ethylferulate is too soft to be micronized neat, and when added unmodified to a formula, ethylferulate alone is very abrasive on skin.

In contrast, when the dispersion described herein is formulated into a sunscreen product, the resulting product has an excellent aesthetic skin feel and a very smooth application on the skin. In addition, the dispersion is efficacious in SPF value relative to the amount of ethylferulate in the formula, and in the dispersed form that results from the inclusion of a solvent, it is even easier to formulate with than the alloy powder which results when no solvent is used. Similar benefits can be realized if a solvent is used in the foregoing methods in which the sunscreen active is an organic liquid or an inorganic substance.

In embodiments in which a solvent is included, and in which the active ingredient is a liquid organic sunscreen active, the lubricating wax is present in an amount ranging from about 20% to about 50% by weight, the sunscreen active is present in an amount ranging from about 20% to about 70% by weight, and the solvent is present in an amount ranging from about 10% to about 60% by weight. In all other respects, the process is the same as set forth above for the use of a solvent with the solid organic sunscreen actives, except that the materials are heated together with stirring to a temperature in the range of 90° C. to 150° C., and preferably in the range of 100° C. to 125° C., until a clear solution is formed. The resulting recrystallized dispersion, which contains very fine droplets of the sunscreen active, spreads smoothly on the skin, feels good when applied, and is comfortable to wear.

In embodiments in which a solvent is included, and the active ingredient is an inorganic sunscreen active, preferably the lubricating wax is first combined with the inorganic sunscreen active to form a solid powder dispersion in the manner described hereinabove in which a solvent is not used. Thereafter, a liquid dispersion of that solid dispersion may be formed, utilizing between about 25% and about 75% by weight, and preferably between about 25% and about 60% by weight, of that solid dispersion, and between about 25% and about 75% by weight, and preferably between about 40% and about 75% by weight, of at least one solvent.

The solvent is charged to a suitable laboratory vessel and is stirred, either at ambient conditions or, if necessary, with the application of heat to a temperature no greater than about 50° C. so as to maintain a stirrable viscosity. The solid powder dispersion is then added slowly, with continued stirring, over a period of between about ten minutes and about thirty minutes, and stirring is prolonged until a uniform dispersion is achieved. If necessary, the latter is then allowed to cool to ambient conditions, yielding in either case a material that is lubricous on the skin and applies smoothly and easily.

In another embodiment in which a solvent is included and the active ingredient is an inorganic sunscreen active, the lubricating wax is first heated with at least one liquid solvent, with stirring, to a temperature within a range of from about 100° C. to about 175° C. to form a solution. At least one inorganic sunscreen active is added, with stirring, while maintaining the temperature range to form a liquid dispersion, which is then cooled.

In embodiments in which a solvent is included, and in which the active ingredient is hydrogenated jojoba, the lubricating wax is present in an amount ranging from about 1% to about 76% by weight, the hydrogenated jojoba is present in an amount ranging from about 1% to about 76% by weight, and the solvent is present in an amount ranging from about 20% to about 80% by weight. These materials are heated together with stirring, to a temperature in the range of from about 70° C. to about 175° C., and preferably from about 70° C. to about 125° C. Alternately, the hydrogenated jojoba may be added subsequent to heating while maintaining the temperature in the elevated range. In all other respects, the process is the same as set forth above for the use of a solvent with the solid organic sunscreen actives.

A further optional refinement in either embodiment of the invention is the addition of at least one fine particle size nucleating agent. The purpose of the nucleating agent is to achieve finer crystal sizes during recrystallization of waxes, wax alloys and wax mixtures and solutions, than would otherwise be achieved in the absence of such an agent or agents. The nucleating agent may also enhance the aesthetic skin feel and other tactile properties of the wax powder alloys and dispersions described above, and may therefore be particularly desirable for use in cosmetics and sunscreens.

The nucleating agent is a material that is insoluble in molten waxes and in molten wax alloys as defined herein in methods in which no solvent is used, or a material that is insoluble in molten solutions and recrystallized dispersions in methods in which a solvent is used. Suitable inorganic nucleating agents include the following: titanium dioxide, zinc oxide, talc, mica, silica, boron nitride and sodium bicarbonate. Organic nucleating agents that are suitable include polytetrafluoroethylene ("PTFE"), polypropylene, hollow microencapsulation beads (such as those obtainable from 3M Company of St. Paul, Minn.), nylon microspheres (such as those obtainable from E. I. du Pont de Nemours & Company of Wilmington, Del.) and other insoluble polyamides.

The mean particle size of such an organic nucleating agent will typically be less than ten microns and preferably about one micron or less, and the mean particle size of such an inorganic nucleating agent will be in the range of from about 20 nanometers to about 100 nanometers for the metallic oxides, and will be less than ten microns, and preferably about one micron or less, for the boron nitride and for the sodium bicarbonate.

The use of one or more nucleating agents in the process of the invention may further enhance the SPF value of the resulting sunscreen product, an effect which is believed due to light scattering induced by the particulate nature of those agents.

In addition to this potential enhancement of the SPF value, a particular improvement in the skin lubricity of the resulting cosmetic and/or sunscreen product has been observed when PTFE is selected as the nucleating agent. Other nucleating agents with known lubricating properties such as the organic nucleating agents listed above, also enhance skin lubricity in the products of the present invention. Titanium dioxide and zinc oxide have also been observed to be effective nucleating agents, and may still further enhance the SPF values of organic sunscreen/wax alloys and mixtures, since as mentioned hereinabove, both titanium dioxide and zinc oxide are also effective inorganic sunblocks. For these reasons the preferred organic nucleating agent is PTFE, and the preferred inorganic nucleating agents are titanium dioxide and/or zinc oxide. It will therefore be evident to those skilled in the art that for certain applications titanium dioxide and zinc oxide can function as nucleating agents and as sunscreen actives in the same formulation.

Typically, the nucleating agent is present in an amount in the range of from about 0.1% to about 30% by weight, and preferably ranging from about 0.1% to about 10% by weight, of the total formula, with the amount of the solvent, in methods in which it is present, being diminished by a corresponding amount to compensate. In the cases in which no solvent is used, the amounts of solid organic wax lubricant and active ingredient may each be diminished approximately equally to compensate for the addition of the nucleating agent.

The nucleating agent is added to the molten wax melt or molten wax mixture or molten wax solution with sufficient stirring to maintain the nucleating agent in a dispersed state, and thereafter the melt or mixture or solution is cooled and hardened, or is rapidly cooled with continued stirring, as the case may be, in the same manner as described hereinabove for a melt or mixture or solution which does not incorporate a nucleating agent. The nucleating agent may be added to the molten wax melt or mixture or solution at any time prior to the cooling thereof. If the nucleating agent is added last, i.e., just prior to the cooling step, then it is preferably added to the melt or mixture or solution over the course of about five minutes.

Alternatively, in cases in which the active ingredient is an organic sunscreen active and in which a solvent is present, the nucleating agent may be added initially to the unheated solvent, preferably over the course of about one to about three minutes (also with stirring to maintain a dispersion), before the solid organic wax lubricant and active ingredient are added to the solvent with heating as described previously. In these cases, sufficient agitation is continually applied to ensure uniform dispersion of the nucleating agent prior to the cooling step, which is subsequently carried out in the same manner as described hereinabove for a molten wax solution that does not incorporate a nucleating agent.

In the foregoing cases in which a solvent is present and the active ingredient is an organic material there may be some instances in which agitation is less than sufficient, such as when the stirrer speed is too slow, to maintain a dispersion of the nucleating agent after the lubricating wax and active ingredient are added. In these instances an alternative pre-dispersion method is preferred for the nucleating agent in which about 10 parts to about 50 parts by weight, and preferably about 20 parts to about 40 parts by weight, of the nucleating agent are added, with stirring, to about 50 parts to about 90 parts by weight, and preferably about 60 parts to about 80 parts by weight, of solvent at ambient conditions, to form a pre-dispersion. An appropriate aliquot of this pre-dispersion is then added to a separately-prepared solution, which is already at elevated temperature and in a stirred state, comprising lubricating wax and active ingredient dissolved in the remainder of the solvent. The pre-dispersion is preferably added to the wax solution over the course of about one to about three minutes, and stirring is continued at elevated temperature for about an additional ten minutes, followed by rapid cooling to induce recrystallization, which again is carried out in the same manner as described hereinabove for a molten wax solution that does not incorporate a nucleating agent.

As is well known in the art, many sunscreen actives, particularly organic sunscreen actives, are heat-sensitive materials, i.e., their ability to absorb ultraviolet light is diminished significantly upon prolonged exposure to heat. Accordingly, although it is within the scope of this invention to heat the active ingredient jointly with the lubricating wax, or jointly with the lubricating wax and solvent, or jointly with the lubricating wax, solvent and nucleating agent, as described hereinabove, and although doing so is preferred when the active ingredient is hydrogenated jojoba or a sunscreen active that is not heat-sensitive (such as the inorganic sunscreen actives, i.e., titanium dioxide or zinc oxide), nevertheless the methods of the invention may also be modified for heat-sensitive sunscreen actives. In cases in which the active ingredient is a heat-sensitive sunscreen active, the other components may be preheated to the required temperature, and thereafter the sunscreen active is added to the molten wax or to the heated solvent solution, as applicable, immediately prior to cooling the resulting mixture. In this manner, the exposure of the sunscreen active to heat is minimized, allowing it to retain more of its expected functional properties in the resulting powder alloy or powder dispersion.

A significant result of utilizing the processes of the present invention is the achievement of very fine particle sizes. In particular, the average size of particles within dispersions formed by the methods of the present invention is substantially reduced as compared with the average size of particles of solid organic sunscreen actives prior to recrystallization by the present method. Yet another significant result is the lubricity of the micronized recrystallized solids and recrystallized dispersions which makes them useful in color formulating industries such as cosmetics and the like. Another significant result of the process is the formation of fine particle size dispersed mixtures. A further significant result is the nucleating effect induced by very fine insoluble additives introduced prior to recrystallization of a solvent solution of waxes. In addition, lubricating wax mixtures of the present invention that contain cosmetic ingredients and sunscreen actives in addition to the wax provide excellent tactile skin feel, excellent skin adhesion and water resistance, and maintain the expected efficacy of the sunscreen active.

Several formulations have been made in laboratory experiments which demonstrate the scope of the various embodiments of the invention and the ingredients employed, and they are set forth as examples which are intended only to be illustrative of the present invention and which are not to be construed as limiting the invention in any manner. In these examples, the amounts of the various ingredients are set forth in parts by weight unless otherwise stated; also, in some of the examples a dispersion was produced, and in those examples the mean particle size of the dispersion was estimated by observing the dispersion in an optical microscope equipped with a dimensional reference grid calibrated in microns.

EXAMPLE 1

A wax powder alloy of oxidized polyethylene and oxybenzone was prepared, using the following ingredients in the following relative amounts.

| oxidized polyethylene | 50% |
|---|---|
| oxybenzone | 50% |

Oxidized polyethylene (Allied Chemical Acuscrub 392), 50 parts, were melted in a laboratory vessel by heating to a temperature in the range of 130° C. to 140° C. over 20 minutes while agitating with a high shear stirrer. Oxybenzone powder, 50 parts, were then added slowly over 20 minutes to the molten oxidized polyethylene while maintaining the temperature at 130° C. to 140° C. The molten wax alloy was then maintained at 130° C. to 140° C. for an additional 5 minutes and stirred with a high shear stirrer to assure a clear and homogeneous melt. The melt was thereafter cast as a thin sheet to assure rapid cooling to 32° C. or less in less than 5 minutes.

The cooled, solid wax alloy was broken up and ground to a coarse powder. This powder was subsequently air jet milled to a mean particle size of 10 microns, suitable for use in a sunscreen formula. The resulting wax alloy powder was finer in particle size than the original oxybenzone and was significantly more lubricous on the skin than oxybenzone alone.

EXAMPLE 2

A wax powder alloy of oxidized polyethylene and ethylferulate was prepared, using the following ingredients in the following relative amounts.

| oxidized polyethylene | 50% |
|---|---|
| Ethylferulate | 50% |

The melt blend was prepared as in the preceding example, except that the oxidized polyethylene was melted over 30 minutes at a temperature in the range of 130° C. to 150° C. The ethylferulate was added slowly, in lump form, and stirred to insure a homogeneous mixture. The molten alloy was cooled, by casting it as a thin sheet, to less than 32° C. in less than 5 minutes. The solid alloy, as cooled above, was too soft for conventional micronization or for fluid energy milling. The alloy was therefore subsequently hardened using a cold sintering process, by storing it at approximately −30° C. for 24 hours, prior to air jet milling. The hardened, solid alloy was subsequently ground and air jet milled to a mean particle size of 14 microns.

The resulting alloy powder had none of the abrasive skin feel of the original ferulic acid ester. When tested for expected SPF value, the alloy maintained efficacy relative to the amount of ethylferulate in the formula.

EXAMPLE 3

A wax powder alloy of ethylenebisstearamide ("EBS") and ethylferulate was prepared, using the following ingredients in the following relative amounts.

| Ethylenebisstearamide | 50% |
|---|---|
| Ethylferulate | 50% |

The melt blend was prepared as in Example 1, except that the EBS (50 parts) was melted over 50 minutes with stirring at 140° C. to 150° C., and the temperature was maintained in that range while the ethylferulate (50 parts) was added. The molten wax mixture was cast as a thin sheet to assure rapid cooling in less than five (5) minutes, and the cooled solid was left to harden over three (3) days, and was subsequently ground and air jet milled to a mean particle size of 3 microns.

The resulting alloy powder had none of the abrasive skin feel of the original ferulic acid ester. The powder was lubricous on the skin and when tested for expected SPF value, the alloy maintained efficacy relative to the amount of ethylferulate in the formula.

EXAMPLE 4

In this example, the procedures and chemical components were the same as in Example 2, except that glycerolmonostearate was substituted for the oxidized polyethylene. The results were similar.

EXAMPLE 5

An improved wax powder alloy of EBS and ethylferulate was prepared, using the following ingredients in the following relative amounts.

| | | |
|---|---|---|
| | Ethylenebisstearamide | 45% |
| | Ethylferulate | 45% |
| | PTFE | 10% |

The melt blend of EBS and ethylferulate was prepared as in Example 3. Thereafter, 10 parts of PTFE were added slowly over 10 minutes to the stirred melt blend. Stirring was continued for an additional 5 minutes and the mixture was then cast as a thin sheet so as to cool rapidly, in less than 5 minutes. The cooled solid was left to harden for one day, and was subsequently ground and air jet milled to a mean particle size of 3 microns.

The resulting wax alloy powder was more lubricous on the skin than the powder of Example 3, and when tested for expected SPF value the alloy maintained efficacy relative to the amount of ethylferulate in the formula.

EXAMPLE 6

A wax alloy dispersion containing EBS and avobenzone was prepared, using the following ingredients in the following relative amounts:

| | | |
|---|---|---|
| | Ethylenebisstearamide | 25% |
| | Avobenzone | 25% |
| | Hydrogenated polyisobutene | 45% |
| | PTFE | 5% |

EBS, 25 parts, polyisobutene, 45 parts, and avobenzone, 25 parts, were added to a laboratory heating vessel and were heated while stirring to a temperature in the range of 130° C. to 150° C. over 30 minutes, to melt and dissolve the wax and avobenzone in the solvent. PTFE, 5 parts, were added slowly over 10 minutes to the stirred, clear molten wax solution. Stirring was continued for an additional 5 minutes, then heat was removed and the hot mixture was cooled rapidly in an ice water bath to less than 32° C. in less than three minutes.

After recrystallization, the resulting wax alloy dispersion had a mean particle size of less than 10 microns.

The resultant dispersion of this example was more lubricous on the skin than the milled powders of prior examples.

EXAMPLE 7

A wax alloy dispersion of EBS and ethylferulate was prepared, using the following ingredients in the following relative amounts.

| | | |
|---|---|---|
| | Ethylenebisstearamide | 20% |
| | Ethylferulate | 30% |
| | Mineral Oil | 20% |
| | Glycerol | 30% |

EBS, 20 parts, ethylferulate, 30 parts, mineral oil, 20 parts, and glycerol, 30 parts, were added to a laboratory heating vessel and were heated to a temperature in the range of 140° C.+/−10° C. over 30 minutes, with stirring, to melt and dissolve the EBS, the sunscreen active and the solvent in the solvent mix. Heat was removed, and the homogeneous solution was cooled rapidly with stirring in an ice water bath to less than 32° C. in less than 3 minutes.

The resulting wax alloy dispersion had a mean particle size of about 3 microns.

EXAMPLE 8

In this example, the procedures and chemical components were the same as in Example 7, except that polydecene was substituted for the solvent mixture of mineral oil and glycerol, and adjustments were made in the relative amounts of the various ingredients, as follows:

| | | |
|---|---|---|
| | Ethylenebisstearamide | 25% |
| | Ethylferulate | 25% |
| | Polydecene | 50% |

The resulting dispersion was similar, but had a mean particle size ranging from about 4 microns to about 5 microns.

EXAMPLE 9

An improved wax alloy dispersion containing EBS and ethylferulate was prepared, using the following ingredients in the following relative amounts.

| | | |
|---|---|---|
| | Ethylenebisstearamide | 25% |
| | Ethylferulate | 25% |
| | Polydecene | 45% |
| | PTFE | 5% |

EBS, 25 parts, polydecene, 45 parts, and ethylferulate, 25 parts, were added to a laboratory heating vessel and were heated to a temperature in the range of 130° C. to 150° C. over 30 minutes, to melt and dissolve the wax and ethylferulate in the solvent. PTFE, 5 parts, were added slowly over 10 minutes to the stirred, clear molten wax solution. Stirring was continued for an additional 5 minutes, then heat was removed and the hot mixture was cooled rapidly in a wiped film heat exchanger to less than 32° C. in less than one minute.

After recrystallization, the resulting wax alloy dispersion had a mean particle size of less than 3 microns; the latter was smaller than the mean particle size of the wax alloy powder of Example 5, which contained the same ingredients except for the solvent, and was also smaller than the particle size range of the wax alloy dispersion of Example 8, which contained the same ingredients except for the nucleating agent. Also, the resultant dispersion of this Example 9 was even more lubricous on the skin than the powder of Example 5, and when tested for expected SPF value the dispersion maintained efficacy relative to the amount of ethylferulate in the formula.

A particular benefit that derives from the inclusion of a solvent in the process of this example, as compared with the processes of Examples 2, 3 and 5, in which the sunscreen active was also ethylferulate but in which no solvent was present, is the facility with which recrystallization from solution takes place, yielding fine particle sizes in less than one minute compared to one or more days in the solid mixtures containing the ethylferulate, where grinding is necessary.

EXAMPLE 10

In this example, the procedures and chemical components were the same as in Example 9, except that erucamide was substituted for the EBS, and the mixture was cooled rapidly to less than 32° C. in less than 3 minutes in an ice water bath. The results were similar, except that the mean particle size in the resulting dispersion was about 4 microns.

EXAMPLE 11

Another improved wax alloy dispersion containing EBS and ethylferulate was prepared using the following ingredients in the following relative amounts.

| | |
|---|---|
| Ethylenebisstearamide | 25% |
| Ethylferulate | 25% |
| Hydrogenated polyisobutene | 45% |
| PTFE | 5% |

Flaked EBS, 25 parts, and hydrogenated polyisobutene, 45 parts, were added to a laboratory heating vessel with stirring. PTFE, 5 parts, were then added slowly at ambient conditions over 10 minutes to the wax and solvent mixture with continued stirring. Thereafter, the mixture was heated to a temperature in the range of 110° C. to 130° C. over 1 hour, with stirring, to melt and dissolve the wax in the solvent.

While maintaining the temperature at 120° C.±10° C., ethylferulate, 25 parts, were added slowly over 10 minutes to the clear molten wax solution, with continued stirring. The ethylferulate was added last to the high-temperature wax solution in order to minimize exposure of the ethylferulate to potential excessive heat. Stirring was continued for an additional 5 minutes, then heat was removed and the hot mixture was cooled rapidly in a wiped film heat exchanger to less than 32° C. in less than one minute.

After recrystallization, the resulting wax alloy dispersion had a mean particle size of less than 3 microns; the latter was smaller than the mean particle size of the wax alloy of Example 5, which contained the same ingredients except for the solvent. Also, the resultant dispersion was particularly more lubricous and pleasant feeling on the skin than the powder of Example 5, and when tested for expected SPF value the dispersion maintained efficacy relative to the amount of ethylferulate in the formula.

EXAMPLE 12

In this example, the procedures and chemical components were the same as in Example 9, except that hydrogenated jojoba was substituted for the ethylferulate, an ice water bath was used for cooling rather than a wiped film heat exchanger (and therefore the cooling time was increased to less than three minutes), and adjustments were made in the relative amounts of the various ingredients, as follows.

| | |
|---|---|
| Ethylenebisstearamide | 20% |
| Hydrogenated jojoba oil | 20% |
| Polydecene | 56% |
| PTFE | 4% |

The resultant dispersion was lubricous on the skin and would be useful as an emollient concentrate.

EXAMPLES 13–15

In these examples, the procedures and chemical components were the same as in Examples 3, 5 and 11, respectively, except that about 10% of hydrogenated jojoba was added to each formula, based on solids, as an emollient, and adjustments were made in the relative amounts of some of the other ingredients, as follows.

| | |
|---|---|
| For Example 13 (as compared with Example 3) | |
| Ethylene bisstearamide | 45% |
| Ethylferulate | 45% |
| Hydrogenated Jojoba | 10% |
| For Example 14 (as compared with Example 5) | |
| Ethylene bisstearamide | 41% |
| Ethylferulate | 41% |
| PTFE | 8% |
| Hydrogenated Jojoba | 10% |
| For Example 15 (as compared with Example 11) | |
| Ethylenebisstearamide | 27% |
| Ethylferulate | 27% |
| Hydrogenated polyisobutene | 35% |
| PTFE | 5% |
| Hydrogenated Jojoba | 6% |

EXAMPLE 16

In this example, the procedures and chemical components were the same as in Example 9, except that octocrylene was substituted for the ethylferulate, and adjustments were made in the relative amounts of the various ingredients, as follows.

| | |
|---|---|
| Ethylenebisstearamide | 30% |
| Octocrylene | 46% |
| Polydecene | 19% |
| PTFE | 5% |

The lubricity of the resultant dispersion was similar.

EXAMPLE 17

A wax alloy dispersion containing EBS and two sunscreen actives, octocrylene and oxybenzone, was prepared, using the same procedures and chemical components as in Example 9, except that adjustments were made in the relative amounts of the various ingredients, as follows.

| | |
|---|---|
| Ethylenebisstearamide | 25% |
| oxybenzone | 12.5% |
| octocrylene | 12.5% |
| Polydecene | 45% |
| PTFE | 5% |

After recrystallization, the resulting wax alloy dispersion had a mean particle size of less than three (3) microns and was lubricous on the skin.

EXAMPLE 18

In this example, the procedures and chemical components were the same as in Example 9, except that octocrylene was substituted for the ethylferulate, and hydrogenated polyisobutene was substituted for the polydecene. After recrystallization, the resulting wax alloy dispersion had a mean particle size of less than three (3) microns and was very lubricous on the skin.

EXAMPLE 19

In this example, the procedures and chemical components were again the same as in Example 9, except that octylmethoxycinnamate was substituted for the ethylferulate. After recrystallization, the resulting wax alloy dispersion had a mean particle size of less than three (3) microns and was very lubricous on the skin.

EXAMPLE 20

A solid powder dispersion of titanium dioxide in ethylenebisstearamide was prepared, using the following ingredients in the following relative amounts.

| | |
|---|---|
| Ethylenebisstearamide | 70% |
| Titanium dioxide | 30% |

Ethylenebisstearamide ("EBS"), 70 parts, were melted in a laboratory vessel over 30 minutes by heating to a temperature in the range of 130° C. to 150° C. using a high speed, high shear stirrer designed for viscous materials. Under constant stirring, 30 parts of sunblock grade titanium dioxide (primary particle size 20–100 nm.) were added slowly over 15 minutes to the molten EBS. Stirring was continued for an additional 15 minutes and the molten dispersion was then poured and cast as a thin sheet for rapid cooling and recrystallization in less than 10 minutes.

The resulting solid dispersion was ground and micronized to a powder which had a mean particle size of approximately 3 microns and was lubricous on the skin. The powder contained titanium dioxide embedded in solid particles of EBS (that are transparent to ultraviolet light) in such a manner that the titanium dioxide could neither migrate nor agglomerate over any reasonable time period.

This material is useful in powder form in sunscreens and in sunscreen-containing cosmetics, especially those which may require a prolonged shelf life. For additional ease of formulation it was dispersed in a liquid in the following manner.

Polydecene, 50 parts, were added to a laboratory vessel and stirred with a high speed stirrer. The micronized powder, 50 parts, was added slowly to the stirred solvent over 20 minutes to form a dispersion. The resulting liquid dispersion of a solid dispersion was more lubricous on the skin and was even easier to formulate with in sunscreens and in cosmetics containing sunscreens.

EXAMPLE 21

In this example, the procedures and chemical components were the same as in Example 20, except that sunblock grade zinc oxide (20–100 nm.) was substituted for the titanium dioxide. The results were similar.

While there has been described what is at present considered to be the preferred embodiments of the present invention, it will be obvious to those skilled in the art that various changes and modifications may be made therein, without departing from the invention.

We claim:

1. A method of making a delivery system for at least one solid or liquid organic sunscreen active, said method comprising the steps of:
   (a) selecting at least one solid organic wax lubricant that is miscible with said at least one sunscreen active at a temperature within a range of from about 70° C. to about 150° C.;
   (b) heating said at least one solid organic wax lubricant to a temperature within said range to form a liquid;
   (c) simultaneous with said heating or subsequent thereto, adding said at least one sunscreen active with stirring while maintaining the temperature of said liquid within said temperature range;
   (d) cooling said liquid to form a substantially solid mixture; and
   (e) milling said solid mixture to form a powder mixture comprising crystals of said at least one solid sunscreen active or droplets of said at least one liquid sunscreen active and crystals of said at least one organic wax lubricant.

2. The method of claim 1 wherein said at least one solid organic wax lubricant is selected from the group consisting of oxidized polyethylene, glycerolmonostearate, candellila wax, carnauba wax, ethylenebisstearamide, montan wax and erucamide.

3. The method of claim 1 or 2 wherein said at least one solid organic sunscreen active is selected from the group consisting of aminobenzoic acid, avobenzone, diethanolamine methoxycinnamate, dioxybenzone, ethyl 4-[bis (hydroxypropyl)] aminobenzoate, ethyferulate, glyceryl aminobenzoate, lawsone with dihydroxyacetone, oxybenzone, phenylbenzimidazole sulfonic acid and sulisobenzone.

4. The method of claim 1 or 2 wherein said at least one liquid organic sunscreen active is selected from the group consisting of cinoxate, digalloyl trioleate, homosalate, methyl anthranilate, octocrylene, octyl methoxycinnamate, octyl salicylate, padimate O, red petrolatum and trolamine salicylate.

5. The method of claim 1 further comprising, prior to said cooling step, the additional step of dispersing in said liquid with stirring at least one nucleating agent selected from the group consisting of titanium dioxide, zinc oxide, talc, mica, silica, boron nitride, sodium bicarbonate, polytetrafluoroethylene, polypropylene, hollow microencapsulation beads and nylon microspheres.

6. A method of making a delivery system for at least one inorganic sunscreen active, said method comprising the steps of:
   (a) selecting at least one solid organic wax lubricant;
   (b) heating said at least one solid organic wax lubricant to a temperature within a range of from about 100° C. to about 175° C. to form a liquid;
   (c) adding said at least one inorganic sunscreen active with stirring while maintaining the temperature of said liquid within said temperature range;
   (d) cooling said liquid to form a substantially solid dispersion; and
   (e) milling said solid dispersion to form a powder comprising crystals of said at least one sunscreen active and crystals of said at least one organic wax lubricant.

7. The method of claim 6 further comprising the steps of:
   (f) selecting at least one liquid solvent; and
   (g) maintaining said solvent at a stirrable viscosity while adding said powder with stirring to form a liquid dispersion comprising crystals of said at least one organic wax lubricant in said at least one solvent, said crystals of said at least one organic wax lubricant having embedded therewithin crystals of said at least one sunscreen active.

8. The method of claim 6 or 7 wherein said at least one solid organic wax lubricant is selected from the group consisting of polyethylene, oxidized polyethylene, polymethylene, polypropylene, glycerolmonostearate, paraffin wax, candellila wax, carnauba wax, ethylenebisstearamide, montan wax, erucamide and microcrystalline wax.

9. The method of claim 6 or 7 wherein said at least one inorganic sunscreen active is selected from the group consisting of titanium dioxide and zinc oxide.

10. The method of claim 6 or 7 further comprising, prior to said cooling step, the additional step of dispersing in said liquid with stirring at least one nucleating agent selected from the group consisting of zinc oxide, talc, mica, silica, boron nitride, sodium bicarbonate, polytetrafluoroethylene, polypropylene, hollow microencapsulation beads and nylon microspheres.

11. A method of making a delivery system for at least one inorganic sunscreen active, said method comprising the steps of:
 (a) selecting at least one solid organic wax lubricant and at least one liquid solvent;
 (b) heating said at least one solid organic wax lubricant and said at least one liquid solvent with stirring to a temperature within a range of from about 100° C. to about 175° C. to form a solution;
 (c) adding at least one inorganic sunscreen active with stirring while maintaining the temperature within said temperature range to form a liquid dispersion; and
 (d) cooling said liquid dispersion.

12. The method of claim 11 wherein said at least one solid organic wax lubricant is selected from the group consisting of polyethylene, oxidized polyethylene, polymethylene, polypropylene, glycerolmonostearate, paraffin wax, candellila wax, carnauba wax, ethylenebisstearamide, montan wax, erucamide and microcrystalline wax.

13. The method of claim 11 wherein said at least one inorganic sunscreen active is selected from the group consisting of titanium dioxide and zinc oxide.

14. A method of making a delivery system for at least one solid or liquid organic sunscreen active, said method comprising the steps of:
 (a) selecting at least one liquid solvent in which said at least one sunscreen active is not readily soluble alone;
 (b) selecting at least one solid organic wax lubricant that is capable of functioning as a cosolvent to enable said at least one sunscreen active to be dissolved readily in said at least one solvent at a temperature within a range of from about 70° C. to about 150° C.;
 (c) heating said at least one solid organic wax lubricant in the presence of said at least one solvent with stirring to a temperature within said range to form a solution;
 (d) simultaneously with said heating or subsequent thereto, adding said at least one sunscreen active to said solution with stirring while maintaining the temperature of said solution within said range; and
 (e) cooling said solution rapidly while stirring to form a powder dispersion comprising crystals of said at least one solid organic sunscreen active or droplets of said at least one liquid organic sunscreen active and crystals of said at least one organic wax lubricant in said at least one solvent.

15. The method of claim 14 wherein said at least one solid organic wax lubricant is selected from the group consisting of oxidized polyethylene, glycerolmonostearate, candellila wax, carnauba wax, ethylenebisstearamide, montan wax and erucamide.

16. The method of claim 14 wherein said at least one solid organic sunscreen active is selected from the group consisting of aminobenzoic acid, avobenzone, diethanolamine methoxycinnamate, dioxybenzone, ethyl 4-[bis(hydroxypropyl)]aminobenzoate, ethyferulate, glyceryl aminobenzoate, lawsone with dihydroxyacetone, oxybenzone, phenylbenzimidazole sulfonic acid and sulisobenzone.

17. The method of claim 14 wherein said at least one liquid organic sunscreen active is selected from the group consisting of cinoxate, digalloyl trioleate, homosalate, methyl anthranilate, octocrylene, octyl methoxycinnamate, octyl salicylate, padimate O, red petrolatum and trolamine salicylate.

18. The method of claim 14 wherein said at least one solvent is selected from the group consisting of glycerine, polydecene, hydrogenated polyisobutene, jojoba oil, dipropyleneglycolmonomethylether, linseed oil, butylcarbitol and petroleum-based fractionated solvents.

19. The method of claim 14 wherein said cooling step comprises cooling said solution from a temperature within said temperature range of from about 90° C. to about 175° C. to a temperature in the range of from about 25° C. to about 50° C. during a period of time in the range of from about 0.01 minutes to about 10 minutes.

20. The method of claim 19 wherein said cooling step comprises cooling said solution in a wiped film heat exchanger.

21. The method of claim 14 further comprising, prior to said cooling step, the additional step of dispersing in said solution with stirring at least one nucleating agent selected from the group consisting of titanium dioxide, zinc oxide, talc, mica, silica, boron nitride, sodium bicarbonate, polytetrafluoroethylene, polypropylene, hollow microencapsulation beads and nylon microspheres.

22. The method of claim 14 further comprising, prior to said heating step, the additional step of forming a separate pre-dispersed mixture by dispersing in said at least one solvent with stirring at least one nucleating agent selected from the group consisting of titanium dioxide, zinc oxide, talc, mica, silica, boron nitride, sodium bicarbonate, polytetrafluoroethylene, polypropylene, hollow microencapsulation beads and nylon microspheres, and wherein said heating step further comprises adding said pre-dispersed mixture to said solution and stirring while maintaining said solution at a temperature within said elevated temperature range.

23. A method for forming a recrystallized powder dispersion of at least one organic solid, said method comprising the steps of:
 (a) dissolving said at least one organic solid in at least one liquid solvent by heating and stirring to form a liquid solution thereof;
 (b) dispersing in said liquid solution with stirring at least one nucleating agent selected from the group consisting of titanium dioxide, zinc oxide, talc, mica, boron nitride, polytetrafluoroethylene, polypropylene, hollow microencapsulation beads and nylon microspheres; and
 (c) cooling said liquid solution while stirring to form a powder dispersion comprising crystals of said at least one organic solid in said at least one solvent, whereby the average size of the particles formed within said dispersion by the crystals of said at least one organic solid is substantially reduced as compared with the average size of the particles of said at least one organic solid prior to said dissolving step.

24. A delivery system for at least one sunscreen active, said delivery system comprising a powder mixture of alloy particulates, said alloy particulates comprising (i) crystals or droplets of at least one organic sunscreen active and (ii) crystals of at least one organic wax lubricant;
 wherein said delivery system is obtained from a method comprising the steps of:
  selecting at least one solid organic wax lubricant that is miscible with said at least one sunscreen active at a temperature within a range of from about 70° C. to about 150° C.;

heating said at least one solid organic wax lubricant to a temperature within said range to form a liquid;

simultaneous with said heating step or subsequent thereto, adding said at least one sunscreen active with stirring while maintaining the temperature of said liquid within said temperature range;

cooling said liquid to form a substantially solid mixture; and milling said solid mixture.

25. The delivery system of claim 24 wherein said at least one organic sunscreen active is selected from the group consisting of aminobenzoic acid, avobenzone, cinoxate, diethanolamine methoxycinnamate, digalloyl trioleate, dioxybenzone, ethylferulate, ethyl 4-[bis(hydroxypropyl)] aminobenzoate, glyceryl aminobenzoate, homosalate, lawsone with dihydroxyacetone, methyl anthranilate, octocrylene, octyl methoxycinnamate, octyl salicylate, oxybenzone, padimate O, phenylbenzimidazole sulfonic acid, red petrolatum, sulisobenzone and trolamine salicylate and wherein said at least one organic wax lubricant is selected from the group consisting of oxidized polyethylene, glycerolmonostearate, candellila wax, carnauba wax, ethylenebisstearamide, montan wax and erucamide.

26. The delivery system of claim 24 further comprising at least one nucleating agent selected from the group consisting of titanium dioxide, zinc oxide, talc, mica, silica, boron nitride, sodium bicarbonate, polytetrafluoroethylene, propylene, hollow microencapsulation beads and nylon microspheres;

wherein said delivery system is obtained from a method comprising the steps of:

selecting at least one solid organic wax lubricant that is miscible with said at least one sunscreen active at a temperature within a range of from about 70° C. to about 150° C.;

heating said at least one solid organic wax lubricant to a temperature within said range to form a liquid;

simultaneous with said heating step or subsequent thereto, adding said at least one sunscreen active with stirring while maintaining the temperature of said liquid within said temperature range;

dispersing in said liquid with stirring said at least one nucleating agent;

cooling said liquid to form a substantially solid mixture; and milling said solid mixture.

27. A delivery system for at least one organic sunscreen active, said delivery system comprising, (A) at least one liquid solvent; and (B) alloy particulates dispersed in said liquid solvent, said particulates comprising, (i) crystals or droplets of at least one organic sunscreen active; and (ii) crystals of at least one organic wax lubricant;

wherein said delivery system is obtained from the method comprising the steps of:

selecting at least one liquid solvent in which said at least one sunscreen active is not readily soluble alone;

selecting at least one solid organic wax lubricant that is capable of functioning as a cosolvent to enable said at least one sunscreen active to be dissolved readily in said at least one solvent at a temperature within a range of from about 70° C. to about 150° C.;

heating said at least one solid organic wax lubricant in the presence of said at least one solvent with stirring to a temperature within said range to form a solution, simultaneous with said heating step or subsequent thereto, adding said at least one sunscreen active to said solution with stirring while maintaining the temperature of said solution within said temperature range; and cooling said solution rapidly while stirring to form said delivery system.

28. The delivery system of claim 27 wherein said at least one organic sunscreen active is selected from the group consisting of aminobenzoic acid, avobenzone, cinoxate, diethanolamine methoxycinnamate, digalloyl trioleate, dioxybenzone, ethylferulate, ethyl 4-[bis(hydroxypropyl)] aminobenzoate, glyceryl aminobenzoate, homosalate, lawsone with dihydroxyacetone, methyl anthranilate, octocrylene, octyl methoxycinnamate, octyl salicylate, oxybenzone, padimate O, phenylbenzimidazole sulfonic acid, red petrolatum, sulisobenzone and trolamine salicylate.

29. The delivery system of claim 27 wherein said at least one organic wax lubricant is selected from the group consisting of oxidized polyethylene, glycerolmonostearate, candellila wax, carnauba wax, ethylenebisstearamide, montan wax and erucamide.

30. The delivery system of claim 27 wherein said at least one solvent is selected from the group consisting of glycerine, polydecene, hydrogenated polyisobutene, jojoba oil, dipropyleneglycolmonomethylether, linseed oil, butylcarbitol and petroleum-based fractionated solvents.

31. The delivery system of claim 27 further comprising at least one nucleating agent selected from the group consisting of titanium dioxide, zinc oxide, talc, mica, silica, boron nitride, sodium bicarbonate, polytetrafluoroethylene, polypropylene, hollow microencapsulation beads and nylon microspheres;

wherein said delivery system is obtained from the method comprising the steps of:

selecting at least one liquid solvent in which said at least one sunscreen active is not readily soluble alone;

selecting at least one solid organic wax lubricant that is capable of functioning as a cosolvent to enable said at least one sunscreen active to be dissolved readily in said at least one solvent at a temperature within a range of from about 70° C. to about 150° C.;

heating said at least one solid organic wax lubricant in the presence of said at least one solvent with stirring to a temperature within said range to form a solution;

simultaneous with said heating step or subsequent thereto, adding said at least one sunscreen active to said solution with stirring while maintaining the temperature of said solution within said temperature range;

dispersing in said solution with stirring said at least one nucleating agent; and cooling said solution rapidly while stirring to form said delivery system.

32. A delivery system for at least one inorganic sunscreen active, said delivery system comprising, (A) at least one liquid solvent;

(B) alloy particulates dispersed in said liquid solvent, said particulates comprising, (i) crystals of at least one organic wax lubricant; and (ii) crystals of at least one inorganic sunscreen active embedded within said crystals of at least one organic wax lubricant;

wherein said delivery system is obtained from a method comprising the steps of:
selecting at least one solid organic wax lubricant;
heating said at least one solid organic wax lubricant to a temperature within a range of from about 100° C. to about 175° C. to form a liquid:
adding said at least one inorganic sunscreen active with stirring while maintaining the temperature of said liquid within said temperature range;
cooling said liquid to form a substantially solid disperson;
milling said solid dispersion to form said alloy particulates;
selecting at least one liquid solvent; and
maintaining said solvent at a stirrable viscosity while adding said alloy particulates with stirring to form said delivery system.

33. The delivery system of claim 32 wherein said at least one inorganic sunscreen active is selected from the group consisting of titanium dioxide and zinc oxide.

34. The delivery system of claim 32 wherein said at least one organic wax lubricant is selected from the group consisting of polyethylene, oxidized polyethylene, polymethylene, polypropylene, glycerolmonostearate, paraffin wax, candellila wax, carnauba wax, ethylenebisstearamide, montan wax, erucamide and microcrystalline wax.

35. The delivery system of claim 32 further comprising at least one nucleating agent selected from the group consisting of titanium dioxide, zinc oxide, talc, mica, silica, boron nitride, sodium bicarbonate, polytetrafluoroethylene, polypropylene, hollow microencapsulation beads and nylon microspheres;
wherein said delivery system is obtained from a method comprising the steps of:
selecting at least one solid organic wax lubricant;
heating said at least one solid organic wax lubricant to a temperature within a range of from about 100° C. to about 175° C. to form a liquid;
adding said at least one inorganic sunscreen active with stirring while maintaining the temperature of said liquid within said temperature range;
dispersing in said liquid with stirring said at least one nucleating agent;
cooling said liquid to form a substantially solid disperson;
milling said solid dispersion to form said alloy particulates;
selecting at least one liquid solvent; and
maintaining said solvent at a stirrable viscosity while adding said alloy particulates with stirring to form said delivery system.

36. The delivery system of claim 27 further comprising at least one nucleating agent selected from the group consisting of titanium dioxide, zinc oxide, talc, mica, silica, boron nitride, sodium bicarbonate, polytetrafluoroethylene, polypropylene, hollow microencapsulation beads and nylon microspheres;
wherein said delivery system is obtained from the method comprising the steps of:
selecting at least one liquid solvent in which said at least one sunscreen active is not readily soluble alone;
selecting at least one solid organic wax lubricant that is capable of functioning as a cosolvent to enable said at least one sunscreen active to be dissolved readily in said at least one solvent at a temperature within a range of from about 70° C. to about 150° C.;
forming a separate pre-dispersion nucleating agent mixture by dispersing in said at least one solvent with stirring said at least one nucleating agent;
heating said at least one solid organic wax lubricant in the presence of said at least one solvent with stirring to a temperature within said range to form a solution;
simultaneous with said heating step or subsequent thereto, adding said at least one sunscreen active and said pre-dispersed nucleating agent mixture to said solution with stirring while maintaining the temperature of said solution within said temperature range; and
cooling said solution rapidly while stirring to form said delivery system.

37. A delivery system for at least one sunscreen active, said delivery system comprising a powder mixture of alloy particulates, said alloy particulates comprising (i) crystals of at least one inorganic sunscreen active and (ii) crystals of at least one organic wax lubricant;
wherein said delivery system is obtained from a method comprising the steps of:
selecting at least one solid organic wax lubricant;
heating said at least one solid organic wax lubricant to a temperature within a range of from about 100° C. to about 175° C. to form a liquid;
adding said at least one sunscreen active with stirring while maintaining the temperature of said liquid within said temperature range;
cooling said liquid to form a substantially solid mixture; and
milling said solid mixture to form said delivery system.

38. The delivery system of claim 37, wherein said at least one inorganic sunscreen active is selected form the group consisting of titanium dioxide and zinc oxide; and wherein said at least one organic wax lubricant is selected from the group consisting of polyethylene, oxidized polyethylene, polymethylene, polypropylene, glycerolmonostearate, paraffin wax, candellila wax, carnauba wax, ethylenebisstearamide, montan wax, eracamide and microcrystalline wax.

39. The delivery system of claim 37 further comprising at least one nucleating agent selected from the group consisting of titanium dioxide, zinc oxide, talc, mica, silica, boron nitride, sodium bicarbonate, polytetrafluoroethylene, propylene, hollow microencapsulation beads and nylon microspheres;
wherein said delivery system is obtained from a method comprising the steps of:
selecting at least one solid organic wax lubricant;
heating said at least one solid organic wax lubricant to a temperature within a range of from about 100° C. to about 175° C. to form a liquid;
adding said at least one sunscreen active with stirring while maintaining the temperature of said liquid within said temperature range;
dispersing in said liquid with stirring said at least one nucleating agent;
cooling said liquid to form a substantially solid mixture; and
milling said solid mixture to form said delivery system.

40. A delivery system for at least one organic sunscreen active, said delivery system comprising,
(A) at least one liquid solvent; and
(B) alloy particulates dispersed in said liquid solvent, said particulates comprising,
(i) crystals or droplets of at least one organic sunscreen active; and (ii) crystals of at least one organic wax lubricant;
wherein said delivery system is obtained from a comprising the steps of:
   selecting at least one solid organic wax lubricant that is miscible with said at least one sunscreen active at a temperature within a range of from about 70° C. to about 150° C.;
   heating said at least one solid organic wax lubricant to a temperature within said range form a liquid;
   simultaneous with said heating step or subsequent thereto, adding said at least one sunscreen active with stirring while maintaining the temperature of said liquid within said temperature range;
   cooling said liquid to form a substantially solid mixture;
   milling said solid mixture to form a powder mixture of alloy particulates;
   selecting at least one liquid solvent; and
   maintaining said solvent at a stirrable viscosity while adding said powder mixture of alloy particulates with stirring to form said delivery system.

41. A delivery system for at least one organic sunscreen active, said delivery system comprising,
   (A) at least one liquid solvent;
   (B) at least one nucleating agent selected from the group consisting of titanium dioxide, zinc oxide, talc, mica, boron nitride, polytetrafluoroethylene, polypropylene, hollow microencapsulation beads and nylon microspheres; and
   (C) alloy particulates dispersed in said liquid solvent, said particulates comprising,
      (i) crystals or droplets of at least one organic sunscreen active;
      (ii) crystals of at least one organic wax lubricant; and
   wherein said delivery system is obtained from the method comprising the steps of:
      dissolving said at least one organic solid in at least one liquid solvent by heating and stirring to form a liquid solution thereof;
      dispersing in said liquid solution with stirring said at least one nucleating agent; and
      cooling said liquid solution while stirring to form said delivery system whereby the average size of the particles formed within said dispersion by the crystals of said at least one organic solid is substantially reduced as compared with the average size of the particles of said at least one organic solid prior to said dissolving step.

42. A delivery system for at least one inorganic sunscreen active, said delivery system comprising,
   (A) at least one liquid solvent;
   (B) alloy particulates dispersed in said liquid solvent, said particulates comprising,
      (i) crystals of at least one organic wax lubricant; and
      (ii) crystals of at least one inorganic sunscreen active embedded within said crystals of at least one organic wax lubricant;
   wherein said delivery system is obtained from the method comprising the steps of:
      selecting at least one solid organic wax lubricant and at least one liquid solvent;
      heating said at least one solid organic wax lubricant and said at least one liquid solvent with stirring to a temperature withing a range of from about 100° C. to about 175° C. to form a solution;
      adding at least one inorganic sunscreen active with stirring while maintaining the temperature within said temperature range to form a liquid dispersion;
      and cooling said liquid dispersion to form said delivery system.

* * * * *